United States Patent [19]

Sakamoto et al.

[11] Patent Number: 4,725,546

[45] Date of Patent: * Feb. 16, 1988

[54] METHOD FOR PURIFICATION OF JAPANESE ENCEPHALITIS VIRUS

[75] Inventors: Kuniaki Sakamoto, Kumamoto; Isao Gotoh; Tetsuo Kawahara, both of Ohzu; Mitsuo Sakoh, Kumamoto, all of Japan

[73] Assignee: Juridical Foundation The Chemo-Sero-Therapeutic Research Institute

[*] Notice: The portion of the term of this patent subsequent to May 7, 2002 has been disclaimed.

[21] Appl. No.: 764,130

[22] Filed: Aug. 9, 1985

[30] Foreign Application Priority Data

Aug. 9, 1984 [JP] Japan .................. 59-167323

[51] Int. Cl.[4] .................. C12N 7/02; C12N 7/00; A61K 39/12
[52] U.S. Cl. .................. 435/239; 435/235; 424/89
[58] Field of Search .................. 435/235, 803, 239; 424/89; 210/927; 530/412, 413

[56] References Cited

U.S. PATENT DOCUMENTS

| | | | |
|---|---|---|---|
| 3,842,062 | 10/1974 | Eastman | 530/411 |
| 3,920,625 | 11/1975 | Andersson et al. | 530/382 |
| 4,138,287 | 2/1979 | Andersson et al. | 435/239 |
| 4,160,019 | 7/1979 | Bjorklund | 436/520 |
| 4,168,300 | 9/1979 | Andersson et al. | 436/514 |
| 4,181,713 | 1/1980 | McAleer et al. | 424/86 |
| 4,434,093 | 2/1984 | Zolton et al. | 252/626 |
| 4,515,714 | 5/1985 | Kawahara et al. | 530/380 |

FOREIGN PATENT DOCUMENTS

| | | | |
|---|---|---|---|
| 49-20322 | 2/1974 | Japan | 424/89 |
| 53-133627 | 11/1978 | Japan | 424/89 |
| 58-79929 | 5/1983 | Japan | 424/89 |

OTHER PUBLICATIONS

Nilsson et al, "Immobilization of Enzymes and Affinity Ligands to Various Hydroxyl Group Carrying Supports Using Highly Reactive Sulfonyl Chlorides", Biochem. and Biophys. Research Comm., 102,(1):449–457, (1981).
Einarsson et al, "A Two-Step Procedure for the Purification of Hepatitis B Surface Antigen (HBsAg)", Vox Sang: 41:91–97, (1981).
Einarsson et al, "Purification of Hepatitis B Surface Antigen by Affinity Chromatography", Vox Sang. 35:224–233, (1978).
Wilchek et al, "Structure of a Soluble Super-Active Insulin is Revealed by the Nature of the Complex Between Cyanogen-Bromide-Activated Sepharose and Amines", Proc. Nat. Acad. Sci. USA, 72,(3):1055–1058, (1975).

Primary Examiner—Esther M. Kepplinger
Assistant Examiner—Shawn P. Foley
Attorney, Agent, or Firm—Fleit, Jacobson, Cohn & Price

[57] ABSTRACT

Disclosed is a method for the purification of Japanese encephalitis virus, which comprises subjecting a solution containing the Japanese encephalitis virus to column chromatography using, as a gel for chromatography, a sulfuric acid ester of cellulose or a crosslinked polysaccharide. The method can provide highly purified Japanese encephalitis virus, which is useful for obtaining an effective vaccine against Japanese encephalitis.

5 Claims, No Drawings

METHOD FOR PURIFICATION OF JAPANESE ENCEPHALITIS VIRUS

BACKGROUND OF THE INVENTION

The present invention relates to a method for the purification of Japanese encephalitis virus, and particularly to such method for obtaining effective vaccines against Japanese encephalitis.

Japanese encephalitis is an infectious disease caused by Japanese encephalitis virus, which attacks animals as well as human beings. The pathogenic virus is known to belong to Arbovirus group and have a spherical shape measuring 35–40 mμ in diameter. The disease generally occurs in Asian areas, particularly in Japan, Korea and Taiwan, and recently in Thailand, Vietnam and India as well. Human patients with Japanese encephalitis may suffer from serious brain injuries and may be led to deaths where the mortality rate is very high. Japanese encephalitis also causes serious conditions on animals. Particularly, pregnant swines infected with the disease often suffer from abortion or stillbirth.

The only possible way for preventing this horrible disease is by vaccination with a vaccine against Japanese encephalitis. In a typical manner for producing a vaccine against Japanese encephalitis, Japanese encephalitis virus is inoculated in the brains of mice and propagated in it. The brain is then subjected to a treatment by which the blood components (particularly hemoglobins) contained therein are removed, followed by the harvest of the propagated virus from the brains of the mice. Then a virus-containing material thus obtained must undergo purification treatments by alcohol precipitation, with protamine sulfate, by ultracentrifugation and/or other techniques, in order to remove the remaining hemoglobins and other contaminants. A typical conventional purification process is carried out as follows:

```
Virus-containing material from the mice brains
    │
    │←── High-speed centrifugation
    ▼
Supernatant         Precipitate
    │
    │←── Addition of protamine sulfate
    │
    │←── High-speed centrifugation
    ▼
Supernatant         Precipitate
    │
    │←── Addition of activated charcoal
    │
    │←── Membrane filtration
    ▼
Virus suspension
    │
    │←── Inactivation with formalin
    ▼
Inactivated-virus suspension
    │
    │←── Ultrafiltration
    │
    │←── Ultra-high-speed centrifugation
    ▼
Supernatnat         Precipitate
                        │
                        │←── Phosphate-buffered sodium
                        │    chloride solution
                        │
                        │←── Gelatine
                        ▼
                      Bulk
                        │
                        │←── Dilution
                        ▼
                    Final Bulk
```

However, as seen from the above, the conventional processes for purification of the virus to produce vaccines against Japanese encephalitis requires the sophisticated and costly techniques with the loss of the vaccine component, and hence improvements thereof are still being requested.

SUMMARY OF THE INVENTION

It is therefore a primary object of the present invention to provide a method by which Japanese encephalitis virus can be purified in a simple and unexpensive manner to produce a Japanese encephalitis vaccine of high purity.

Other objects and features of the present invention will be apparent from the following description.

The present invention is based on the discovery that a sulfuric acid ester of cellulose or a crosslinked polysaccharide has a specific affinity with Japanese encephalitis virus, and is effective for isolation and purification of the virus from a material containing the same. Thus, according to the present invention, there is provided a method for the purification of Japanese encephalitis virus which comprises subjecting a solution containing the virus to column chromatography using, as a gel for chromatography, a sulfuric acid ester of a crosslinked polysaccharide or cellulose.

The sulfuric acid ester of cellulose to be used in the present invention includes a sulfuric acid ester of crystalline cellulose or cellulose having crystalline area and non-crystalline area. These starting celluloses are commercially available, for example, as Abicel (manufactured by Asahi Kasei in Japan), Cellulofine GC-15, GH-25 GC-100, or GC-200 (manufactured by Chisso Corp. in Japan).

The sulfuric acid ester of a crosslinked polysaccharide to be used in the present invention includes a sulfuric acid ester of polysaccharides, such as dextran, cellulose, agarose, which is crosslinked with a crosslinked agent, such as epichlorohydrin, dichlorohydrin, dibromohydrin, ethylene glycol bisepoxypropyl ether. The crosslinked polysaccharides are commercially available, for example, as crosslinked dextran such as Sephadex G-10, G-25, G-50, and G-100 (manufactured by Pharmacia in Sweden), crosslinked agaroses such as Sepharose Cl-2B, Cl-4B, and Cl-6B (manufactured by Pharmacia in Sweden), and crosslinked celluloses such as Cellulofine GCL-25, GCL-90 (manufactured by Chisso Corp. in Japan).

The sulfation of such crosslinked polysaccharide or cellulose can be carried out by a conventional method. However, the gel for chromatography to be used in the present invention is characterized in that it is prepared by directly sulfating cellulose or a crosslinked polysaccharide, which are water-insoluble, with a sulfating agent such as chlorosulfonic acid or anhydrous sulfuric acid in an organic solvent (e.g. pyridine). Thus, the resultant gel is water-insoluble and highly stable. Further, such gel of the sulfuric acid ester of cellulose or a crosslinked polysaccharide exhibits an extremely high adsorbing activity since it is fully sulfated, even at the inner regions thereof. The use of the gel is also advantageous from an economical standpoint, because it can be easily prepared at a low cost. The degree of sulfation (content of the sulfonyl group) of crosslinked polysaccharide is usually in the range of 0.1 to 40%, preferably 10 to 40%, based on the weight of the crosslinked polysaccharide, and the degree of sulfation of cellulose is usually in the range of 0.1 to 5.0%, based on the cellulose.

The procedure of purification of Japanese encephalitis virus by column chromatography using the sulfuric acid ester of a crosslinked polysaccharide or cellulose is carried out in a similar manner to that in the conventional column chromatography. For instance, the method is carried out in the following manner: First, a sulfuric ester of a crosslinked polysaccharide or cellulose (preferably, in the form of spherical particles) is packed within a column, which is equilibrated with a suitable buffer solution, preferably having an ionic strength of about 0.001 to 2.0, for example, 0.01M phosphate buffered saline sulution containing 0.14M NaCl (pH 7.0–8.0). After the equilibration, a Japanese encephalitis viruscontaining solution to be treated is passed through the column in order to adsorb such virus onto the gel, followed by washing with the same buffer solution as used for the above equilibration. Thereafter, the adsorbed virus is eluted from the column by passing through the column a suitable buffer solution having an ionic strength larger than that of the buffer solution used for the equilibration or the washing, for example, 1.0M to 1.5M sodium chloride-containing phosphate buffer solution (pH 6–9) to give desired highly purified Japanese encephalitis virus.

The method of the present invention can be applied to any solution containing Japanese encephalitis virus and can be conducted at any stage in the purification of Japanese encephalitic virus. Thus, the method can be applied to a solution containing Japanese encephalitis virus before being subjected to an inactivation treatment as well as an inactivated Japanese encephalitis virus-containing solution. For example, the virus suspension obtained by the conventional purification process, as described in the above, undergoes the method of the present invention in order to clarify Japanese encephalitis contained therein. An inactivated Japanese encephalitis virus-containing solution, such as the inactivated-virus suspension as described above, can also be subjected to the method of the invention for purifying the virus. In any case, Japanese encephalitis virus can specifically adsorb onto the sulfate gel. Thus, according to the method of the present invention, Japanese encephalitis virus can be highly purified, without the need for the troublesome pretreatment to remove the blood components (hemoglobins) originating from the brains of mice. Furthermore, the present invention can be applied to a Japanese encephalitis virus-containing solution produced by any other process, for example, that obtained by propagating the virus in a culture cell such as the culture cell of hamster kidney. The method of the present invention may also be applied to a solution containing Japanese encephalitis virus proteins which would be expressed by means of genetic engineering.

According to the purification method of the present invention, Japanese encephalitis virus can be purified in a high degree, with the least contamination with proteins, lipids and other substances resulting from the mice used and/or the culturing medium. This is probably due to the fact that the sulfonyl group bonds directly to the crosslinked polysaccharide or cellulose in the sulfuric acid ester of a crosslinked polysaccharide or cellulose and hence it has a high content of sulfonyl group and shows excellent specific adsorbability to Japanese encephalitis virus. The purification method of the present invention can be easily done with simple operation without need for expensive techniques and give the desired purified Japanese encephalitis virus on an industrial scale with lower cost. If desired, the method of the present invention can be combined with conventional separation techniques (e.g. ultracentrifugation) so as to obtain Japanese encephalitis virus as highly as possible.

The present invention will now be illustrated by the following Preparations (preparations of gels for chromatography) and Examples, but should not be construed to limited thereto.

PREPARATION 1

To pyridine (600 ml) is added dropwise chlorosulfonic acid (117 g) at below 0° C. After the addition, the mixture is heated to 65°–70° C. To the mixture is added crystalline cellulose gel (Cellulofine GC-15, manufactured by Chisso Corp.) (80 g), and the mixture is stirred at 65°–70 °C. for 3 hours. After the completion of the reaction, the mixture is cooled and neutralized with 10% aqueous sodium hydroxide. The gel thus obtained is separated by filtration and washed thoroughly with 0.01M phosphate buffer-aqueous sodium chloride mixture to give a cellulose sulfate gel.

PREPARATION 2

To pyridine (600 ml) is added dropwise chlorosulfonic acid (117 g) at below 0° C. After the addition, the mixture is heated to 65°–70° C. To the mixture is added crystalline cellulose (Abicel for chromatography, munufactured by Asahi Kasei) (80 g), and the mixture is stirrred at 65°–70° C. for 4 hours. After the completion of the reaction, the mixture is cooled and then neutralized with 10% aqueous sodium hydroxide. The gel thus obtained is separated by filtration and washed thoroughly with 0.01M phosphate buffer-aqueous sodium chloride mixture to give a cellulose sulfate gel.

PREPARATION 3

To pyridine (200 ml) is added dropwise chlorosulfonic acid (11 ml) at below 0° C. After the addition, the mixture is heated to 65°–70° C. To the mixture is added epichlorohydrin-crosslinked dextran (Sephadex G-50, manufactured by Pharmacia) (7.5 g), and the mixture is stirred at 65°–70° C. for 4 hours. After the reaction, the reaction mixture is cooled and then neutralized with aqueous sodium hydroxide. The gel thus obtained is separated by filtration and washed thoroughly with 0.01M phosphate-buffered saline solution to give a crosslinked dextran sulfate.

EXAMPLE 1

The cellulose sulfate gel obtained in the manner as described in Preparation 1 is packed within a column (25 mm$\phi$×400 mm), followed by the passage of 375 ml of distilled water through the column. The packed column is equilibrated with 0.01M phosphate-bufferd saline solution containing 0.14M sodium chloride. Then, through the column is packed 50 ml of an inactivated Japanese encephalitis virus-containing suspension obtained by the process as described in the above along the chart. After the passage of the virus-containing solution, the column is fully washed with 0.01M phosphate buffer solution containing 0.14M sodium chloride. Then, the adsorbed material is eluted with 100 ml of 0.01M phosphate buffer solution containing 1.5M sodium chloride (specific conductivity 120 mS/cm, pH 7.2). The staring solution and the eluate are determined with respect to the respective virus contents in terms of HA (Hemagglutinin) titer. The results are shown in Table 1, which demonstrates that the virus contained in the starting solution is recovered substantially with 100%.

TABLE 1

| Virus content (HA titer) | |
|---|---|
| Starting Solution | Eluate |
| 1,600 | 1,536 |

EXAMPLE 2

Using the cellulose sulfate gel obtained in Preparation 2, a procedure is conducted similar to Example 1 except that there is used, as a starting solution, 50 ml of a supernatant just before the addition of activated charcoal in the process as described in the above (a solution before the inactivation). The results are summarized in Table 2, which also demonstrates substantially all the virus can be recovered by the method of the invention.

TABLE 2

| Virus content (HA titer) | |
|---|---|
| Starting solution | Eluate |
| 3,200 | 3,072 |

EXAMPLE 3

Using the cellulose sulfate gel obtained in Preparation 1, a purification procedure is conducted in a similar manner to that in Example 1, except that there is passed 1,000 ml of a Japanese encephalirtis virus-containing suspension (a solution just before the inactivation treatment), through the column (500 mm$\phi$×2,500 mm). The virus contents are determined in the same manners as in Example 1, with the results shown in Table 3, which also demonstrates all the virus contained in the starting solution can be recovered.

TABLE 3

| Virus content (HA titer) | |
|---|---|
| Starting Solution | Eluate |
| 16,000 | 20,480 |

EXAMPLE 4

Using the crosslinked dextran sulfate gel obtained in the manner as described in Preparation 3, the purification of an inactivated Japanese encephalitis virus-containing suspension, the same as used in Example 1, is carried out in the same manner as in Example 1, with the results shown in Table 4.

TABLE 4

| Virus content (HA titer) | |
|---|---|
| Starting solution | Eluate |
| 1,600 | 1,572 |

What is claimed is:

1. A method for the purification of Japanese encephalitis virus, which comprises subjecting a solution containing the Japanese encephalitis virus to column chromatography using, as a gel for chromatography, a sulfuric acid ester of the cellulose or a crosslinked polysaccharide, said sulfuric acid ester being prepared by treating a gel of cellulose or crosslinked polysaccharide with a sulfating agent in an orgainic solvent.

2. The method as claimed in claim 1, wherein the Japanese encephalitis virus-containing solution is one containing an inactivated Japanese encephalitis virus.

3. The method as claimed in claim 1, wherein the Japanese encephalitis virus-containing solution is one containing non-inactivated encephalitis virus.

4. The method as claimed in claim 1 wherein the sulfuric acid ester of a crosslinked polysaccharide is selected from the group consisting of a crosslinked cellulose sulfate, a crosslinked agarose sulfate and a crosslinked dextran sulfate.

5. The method as claimed in claim 1 wherein the sulfuric acid ester of cellulose is a sulfuric acid ester of crystalline cellulose or a cellulose having a crystalline area and non-crystalline area.

* * * * *